US009279788B2

(12) United States Patent
Liu

(10) Patent No.: US 9,279,788 B2
(45) Date of Patent: Mar. 8, 2016

(54) APPARATUS AND METHODS FOR PREPARATIVE LIQUID CHROMATOGRAPHY

(71) Applicant: Waters Technologies Corporation, Milford, MA (US)

(72) Inventor: Hongji Liu, Grafton, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 14/672,746

(22) Filed: Mar. 30, 2015

(65) Prior Publication Data

US 2015/0204826 A1    Jul. 23, 2015

Related U.S. Application Data

(60) Division of application No. 12/278,287, which is a continuation of application No. PCT/US2007/061586, filed on Feb. 5, 2007, now Pat. No. 8,992,778.

(60) Provisional application No. 60/771,545, filed on Feb. 8, 2006.

(51) Int. Cl.
*G01N 30/16* (2006.01)
*G01N 30/34* (2006.01)
*G01N 30/02* (2006.01)

(52) U.S. Cl.
CPC ............... *G01N 30/16* (2013.01); *G01N 30/34* (2013.01); *G01N 2030/027* (2013.01); *G01N 2030/347* (2013.01)

(58) Field of Classification Search
CPC ................. G01N 30/34; G01N 2030/347
USPC .............. 210/656, 659, 101, 137, 143, 198.2
See application file for complete search history.

(56) References Cited

U.S. PATENT DOCUMENTS

| | | |
|---|---|---|
| 5,158,675 A | 10/1992 | Allington et al. |
| 6,139,734 A | 10/2000 | Settlage et al. |
| 6,402,946 B1 | 6/2002 | Spraul et al. |
| 6,780,315 B2 * | 8/2004 | Richardson et al. ....... 210/198.2 |
| 6,858,435 B2 | 2/2005 | Chervet et al. |
| 6,955,760 B2 | 10/2005 | Iwata |
| 7,396,469 B2 | 7/2008 | Andrews et al. |
| 2004/0108273 A1 | 6/2004 | Richardson et al. |
| 2005/0098487 A1 | 5/2005 | Ito |
| 2006/0186028 A1 | 8/2006 | Hughes |

(Continued)

FOREIGN PATENT DOCUMENTS

| | | |
|---|---|---|
| EP | 1544612 | 6/2005 |
| WO | 2007109157 | 9/2007 |

OTHER PUBLICATIONS

GB Examination Report for GB0814554.2, dated Apr. 21, 2010.

(Continued)

*Primary Examiner* — Ernest G Therkorn
(74) *Attorney, Agent, or Firm* — Waters Technologies Corp.

(57) ABSTRACT

Embodiments of the present invention feature methods and apparatus for performing chromatographic separations. The invention feature methods and control means in the form of computer programs and software that control the formation of a concentration gradient at two or more total flow rates, with an elution period occurring in a slow flow rate and at least other portions of the gradient occurring during a fast total flow rate.

18 Claims, 4 Drawing Sheets

(56) References Cited

U.S. PATENT DOCUMENTS

| | | | |
|---|---|---|---|
| 2006/0219618 | A1 | 10/2006 | Witt et al. |
| 2007/0183928 | A1* | 8/2007 | Neyer et al. .................... 422/70 |
| 2007/0199874 | A1 | 8/2007 | Ito et al. |
| 2009/0205409 | A1 | 8/2009 | Ciavarini et al. |
| 2009/0294363 | A1 | 12/2009 | Liu |

OTHER PUBLICATIONS

GB Examination Report for GB0814554.2, dated Nov. 11, 2010.
GB Examination Report for GB1013956.6, dated Nov. 11, 2010.
PCT International Search Report for Application No. PCT/US07/61586, Form PCT/ISA/220 + 210, date of completion Aug. 24, 2007.
PCT International Written Report for Application No. PCT/US07/61586, Form PCT/ISA/237, date of completion Aug. 24, 2007.
Davis, et al., "Capillary Liquid Chromatography/Mass Spectrometry for Peptide and Protein Characterization"; Methods: A Companion to Methods in Enzymology V6,304-314 (1994).
Schwartz, et al., "Gradient elution for micro HPLC"; Liquid Chromatography, (1985) V3, No. 2,110-124.
Snyder, et al., "Introduction to Modern Liquid Chromatography"; 2nd ed., A Wiley-Interscience Pub, (1979) 662-719.
Snyder, et al., "Introduction to Modern Liquid Chromatography"; 2nd ed., A Wiley-Interscience Pub, (1979) 83-124.
Berry, et al., "Low-Cost Liquid Chromatography (LC-LC). IV. "Pulsed Open Tube Gradient Generation", A new Approach for Generating Nanoliter vol. Linear and Tailored Gradients for Capillary Electrophoresis and Micro-LC"; Journal of Liquid Chromatography & Related Technologies, (1990) 13:8,1529-1558.
Katz, et al., "Liquid Chromatography System for Fast, Accurate Analysis"; Journal of Chromatography, (1982) 253 159-178.
Natsume, et al., "A Direct Nanoflow Liquid Chromatography—Tandem Mass Spectrometry System for Interaction Proteomics"; Anal. Chem., (2002) 74, 4725-4733.
Quarry, et al., "Measurement and Use of Retention Data from High-Performance Gradient Elution (Contributions from "Non-Ideal" Gradient Equipment)"; Journal of Chromatography, (1984) 285, 1-18.
Rapp, et al., "Liquid flow in capillary (electro) chromatography:Generation and control of micro- and nanoliter volumes"; J. Sep. Sci. (2003) 26, 453-470.
Schachterle, et al., "Preformed Gradient Technique for Microbore High-Performance Liquid Chromatography"; Anal. Chem., (1986) 58, 1368-1372.
Schwartz, et al., "Gradient Elution Chromatography with Microbore Columns"; Anal. Chem., (1983), 55, 1752-1760.
Scott, et al., "Use of Microbore Columns for the Separation of Substances of Biological Origin"; Journal of Chromatography, (1979) 185, 27-41.
Swartz, "UPLC: An Introduction and Review"; Journal of Liquid Chromatography & Related Technologies, (2005) 28:7, 1253-1263.
van der Wal, et al., "Gradient Elution System for Capillary and Micro HPLC"; J. High Res. Chrom. & Chrom. Commun., (1983) 6, 216-217.
Snyder, "An Experimental Study of col. Efficiency in Liquid-Solid Adsorption Chromatography (HETP Values as a Function of Separation Conditions)"; Anal. Chem., (1967), 39:7, 698-704.
Halasz, et al., "Different Types of Packed Columns in Liquid-Solid Chromatography"; Journal of Chromatographic Science, (1969) V7, 129-136.
Huber, et al., "A study of liquid chromatography in columns. The time of separation"; Anal. Chim. Acta, 38, (1967) 305-313.
Snyder, et al., "Optimized Solvent Programming for Separations of Complex Samples by Liquid-Solid Adsorption Chromatography in Columns", pp. 289-302, undated.
Nice, et al., "The role of short microbore high-performance liquid chromatography columns for protein separation and trace enrichment"; Journal of Chromatography, 296 (1984) 153-170.
Ishii, et al., "The 204 Chromatograph expansion plan"; Journal of Chromatography, 144 (1977) 157-168.
Takeuchi, et al., "Continuous gradient elution in micro high-performance liquid chromatography"; Journal of Chromatography, 253 (1982) 41-47.
Abstract of JP 60183553 dated Sep. 19, 1985 by Tetsuyuki.
Abstract of JP 2004101477 dated Apr. 2, 2004 by Yoshio.
Abstract of JP 2002071657 dated Mar. 12, 2002 by Minoru.
Schwartz, et al., " Comparison of Dynamic and Static Mixing Devices for Gradient Micro-HPLC"; Journal of Chromatographic Science, V23, Sep. 1985, 402-406.

* cited by examiner

APPARATUS AND METHODS FOR PREPARATIVE LIQUID CHROMATOGRAPHY

CROSS REFERENCE TO RELATED APPLICATIONS

This application is a divisional of U.S. application Ser. No. 12/278,287 filed on Jun. 8, 2009, now U.S. Pat. No. 8,992,778 which is a 371 of and the National Stage of International Application No. PCT/US2007/061586 filed on Feb. 5, 2007, which claims priority to and benefit of U.S. Provisional Patent Application No. 60/771,545, filed Feb. 8, 2006. The entire contents and teachings of each of these applications are hereby expressly incorporated herein by reference in their entirety.

FIELD OF THE INVENTION

This invention relates to apparatus and methods for generating solvent gradients. Solvent gradients are used in gas and liquid chromatography.

BACKGROUND OF THE INVENTION

Chromatography is an analytical technique for separating a mixture into its constituents. The mixture containing compounds is moved through a stationary phase. The compounds held in the mixture, the mobile phase, exhibit different affinity for the stationary phase. The compounds are thus retained or allowed to pass at different rates as the mobile phase moves producing bands or peaks of the compounds in the stationary phase or exit the stationary phase at different times.

Gas chromatography uses one or more mixtures comprising a gas as a solvent to carry sample compounds to be analyzed. Liquid chromatography uses one or more mixtures of liquids as a solvent. Supercritical fluid chromatography uses one or more gases held at pressures and temperature in which the gas takes on one or features of liquids as a solvent. This document will use the term "fluid" to means gases, liquids and supercritical fluids.

A common form of liquid chromatography, high performance liquid chromatography (HPLC), uses pressure to propel liquids through a stationary phase. In a typical HPLC analysis, a solvent (mobile phase) is pumped through a column packed with a solid porous material (stationary phase). A sample is injected into the solvent and compounds in the sample are adsorbed on the stationary phase. This step of placing the sample in the stationary phase is referred herein as "loading". Each compound exhibits different affinity to the stationary phase so that they exit the column separated in time. The step or process of leaving the stationary phase is referred herein as "elution" and the materials leaving the stationary phase are referred to as the "eluant." A detector receives the column eluent and generates an electrical signal indicative of the presence of compounds in the sample. A mass spectrometer is frequently used as a detector because it may provide detailed information about the chemical identity of the compounds.

Chromatographers desire an efficient separation with respect to the time taken for a separation, materials consumed and the degree of separation. Efficiency may be increased and the time reduced by gradient elution, in which a mixture of two or more solvents is used as the mobile phase. The proportions of the two solvents is varied as the separation proceeds, typically to change the polarity to change the interaction of the compounds with the stationary phase. A change of the proportions of the two solvents may cause one or more compounds to elute and thereby shorten the retention time for such compounds.

Method of generating solvent gradients with a variety of pump means comprising multiple pumps, single pumps with proportioning valves are known in the art. See: Berry, Schwartz, J. Chrom. Sci. 1989 vol. 45 pp 67-116, the contents of which are incorporated herein by reference.

The quest for better sensitivity has led to the use of even smaller diameter columns employing even smaller particle sizes. Such columns require pumps capable of producing very low stable flows at very high pressures. For example, current column technology (known as nanoflow) may use a 75 µm diameter capillary column, and particles of 1.7 µm diameter, requiring a flow often less than 500 nl/minute at a pressure as high as 8000 psi.

When gradient elution is performed at low flow rates, the delay between the initiation of the gradient by the pumps and the time at which it appears at the column inlet, referred herein as "gradient delay", becomes a major cause of extended analysis times. For example, if the dead volume of the connections between the pumps, sample injection valve and the column inlet is 5 µl, at a flow rate of 250 nl/minute, there is a gradient delay of twenty minutes. During the twenty minutes of delay, sample is not presented to the detector and the detector is not generating data. Some detectors are very expensive, such as mass spectrometers.

It is desirable to maximize the amount of sample presented to such detectors to generate data as efficiently as possible.

SUMMARY OF THE INVENTION

Embodiments of the present invention feature methods and apparatus for efficiently performing gradient elution. The greater efficiency of the chromatographic separation allows detectors to receive more samples and generate more data. One embodiment of the present invention is directed to a device for performing chromatographic separations.

The device has pump means, fluid conveying means, sample injection means, separation means and control means. The pump means propels a first solvent and a second solvent to form a range of mixtures having a different concentration of the first solvent and the second solvent. The range of mixtures produced by the pump means over time define a concentration gradient. The movement of the first solvent and second solvent define a total flow rate capable of being changed over time.

The fluid conveying means is in fluid communication with the pump means for receiving the first solvent and the second solvent. The fluid conveying means has a length and a diameter defining a volume through which the first solvent and the second solvent flow, as a mixture if both first solvent and second solvent are present. The pump means is capable of forming a concentration gradient along at least a portion of the length in this volume. As used herein, fluid conveying means refers to piping, tubing, capillaries, and associated fittings, unions, couplers, "T" unions, valves and the like. The term "fluid communication" refers to components plumbed together.

The sample injection means is in fluid communication with the fluid conveying means for placing a sample in at least one of the first solvent and the second solvent flowing through the fluid conveying means. As used herein, "sample injection means" refers to a port, sample loop, valve, "T" union, autosampler assembly and the like.

The separation means is in fluid communication with the fluid conveying means. The separation means comprises at least one separation media for receiving the sample and at least one of the first solvent and the second solvent. At least one solvent or one range of concentration gradient is a loading gradient in which the sample or compounds of the sample are loaded on the separation media. And, at least one range of concentration gradient is an elution gradient in which one or more compounds are separated over time or in response to changes in the concentration of said first and second solvent, the time in which the elution gradient is performed is an elution period. And, at least one solvent or one range of concentration gradient is a utility gradient in which the compounds are conveyed to the separation means, or the separation means are conditioned for sample. The loading gradient and utility gradient may therefore form part of the concentration gradient with the same or different rate of change or be a static period in which the concentrations of one or more solvent remain substantially unchanged. Separation means refers to columns, extraction cartridges, and other in-line closed devices. Separation media refers to particles, porous monolith materials, and other packings known in the art.

The control means is in signal communication with the sample injection means and the pump means for controlling the total flow rate and formation of said concentration gradient. The term "signal communication" refers to components sending and receiving electric-magnetic or optical signals over wire or through wireless transmission. The control means, in response to the injection of the sample or the anticipated timing of the injection of said sample, determines and forms at least one concentration gradient in the volume at a fast total flow rate and at a slow total flow rate such that the elution gradient passes through the separation media during an elution period in the slow total flow rate, and at least one of the utility gradient and the loading gradient occurs during a fast period in the fast total flow rate.

As used herein, control means refers to one or more computer processing units (CPUs), personal or main frame computers equipped with suitable software or firmware. The drafting of such software programs for analytical instruments is within the skill of a computer software engineer. Such software is a set of programmed queries and commands which process data, activate hardware, and monitor signals.

Embodiments of the present invention use volumes normally associated with delay, that is such volumes in the fluid conveying means, to build and store concentration gradients. At slow flow rates, such delays, often referred to as gradient delays, can be substantial.

A preferred embodiment of the present invention has control means that automatically determines a fast period and the elution period for a linear gradient performed between Bx to By in accordance with the following relationships:

$$T_{qgd} = V_d / F_{qgd} \quad \text{(Formula I)}.$$

As used above, $T_g$ is the time at said slow total flow rate of $F_g$ to complete the linear gradient between Bx and By. The designations, is used to denote Bx as the lowest, and, By, the highest concentration in percentage, of a selected solvent selected from the group of the first solvent and second solvent. The letter designation, $T_{qgd}$, is the time needed to perform said fast period. The letter designation, $V_d$, is the volume of the fluid conveying means and $F_{qgd}$ is the flow rate of the fast period. And, the control means determines $B_{qgd}$, the highest concentration of the selected solvent to be delivered during the fast period, in accordance with Formula II, set forth below:

$$B_{qgd} = [V_d(B_y - B_x)/F_g T_g] + B_x \quad \text{(Formula II)}.$$

And, the slow period, $T_2$, in which the elution period will take place, is determined by Formula III below:

$$T_2 = T_g - (V_d / F_g) \quad \text{(Formula III)}$$

And, the time to complete the fast period, $T_{combined}$, is determined with the following Formula IV:

$$T_{combined} = T_2 + T_{qgd} \quad \text{(Formula IV)}.$$

A preferred embodiment of the device has control means that uses a value of $V_d$ selected from the group of values consisting of an assigned value and a calculated value. For example, a preferred control means has memory commonly associated with computers and CPUs, such as hard-drives, memory chips and other memory devices. An assigned value or a calculated value is stored in such memory. The assigned value can be approximated based on internal measurements of the fluid conveying means and stored in the memory during a manufacturing process.

One embodiment of the present invention features a calculated value determined by the relationship, as set forth below:

$$V_d = F_c(T_{c1} - T_{c2}) \quad \text{(Formula IV)}.$$

As used above, $F_c$ is the flow rate at a stable back pressure of a high percentage concentration of the second solvent represented by $B_{high}$; and $T_{c1}$ is the time at which such second solvent is changed to a low percentage concentration $B_{low}$ and $T_{c2}$ is the time that the back pressure at such low percentage concentration becomes stable. One embodiment of the present invention features control means that calculates a value of $V_d$ upon receiving instructions to do so from an operator, or automatically, when the operator designates a fast gradient operation, or if there is no preset value which the control means can use.

To facilitate the calculation of the value of $V_d$ one embodiment features at least one of the pump and fluid conveying means having a pressure sensors. The pressure sensor is in signal communication with the control means to measure pressure in the fluid components.

Embodiments of the present invention can operate at fast total flow rates four to one hundred times the flow rates of slow total flow rates. At such flow rates, the pump and the fluid conveying means may develop high pressures. On embodiment of the present invention features a device having a maximum safe operating pressure. And, the pressure sensor produces a signal in respond to pressures greater than such safe operating pressure.

One embodiment features a control means that calculates an anticipated pressure for the fast total flow rate and compares the anticipated pressure to a safe operating pressure value. Preferably, the control means produces a stop signal in response to the anticipated pressure exceeding said safe operating pressure value.

Embodiments of the present device are well suited for handling a plurality of samples in an automated manner. For example, the control means is programmed to repeat the concentration gradient for a plurality of samples in which each concentration gradient is a gradient cycle substantially next to at least one preceding or subsequent concentration gradient in the fluid conveying means.

One embodiment of the present device features an exit port. The exit port is fluid communication with the fluid conveying means and is in signal communication with the control means. The exit port has an open position and a closed position. In the closed position, the exit port directs the first solvent, second solvent and, if present, sample, to the separation means. And, in the open position, the port directs the first solvent, second solvent and, if present, sample, to waste.

Embodiments of the present invention are well suited for use with separation means comprising a trapping column and an analytical column. As used herein, the term trapping column refers to a separation column or cartridge having a packing or monolithic separation media. Trapping columns are typically shorter columns used to initially capture or "trap" compounds of interest. An analytical column is usually a longer column in which compounds are separated.

Preferably, the device further comprises a solvent port in fluid communication with said fluid conveying means and in signal communication with said control means. The solvent port is preferably upstream from the trapping column and is in fluid communication with a third solvent which solvent is capable of releasing the compound or compounds of interest from the trapping column. The released compound or compounds are carried to the analytical column which analytical column effects separation.

Preferably, the control means sends a release signal to the solvent port to release the third solvent. And, preferably, the control means begins said elution period after the release signal.

Embodiments of the present invention are suited for use with detection means in fluid communication with said separation means. The detection means receives the sample or compounds of the sample and produces a analytical signal. The term "analytical period", as used herein, refers to the time in which said detection means receives sample or compounds of the sample. The detection means may assume any number of detectors known in the art. By way of example, without limitation, detection means may comprise photodetectors, such as photodiode array detectors, Ramon light detectors, light scattering detectors, light absorbance detectors, fluorescence detectors, chemiluminescent detectors, or electrochemical detectors, mass detectors, nuclear magnetic resonance detectors and others.

A further embodiment of the present invention is directed to a method of performing chromatographic separations. The method comprising the steps of providing a device as described in any of the embodiments above and operating the device to produce a concentration gradient at a fast total flow rate and a slow total flow rate in response to the injection of said sample or the anticipated injection of said sample. The present method performs the step of elution during an elution period at the slow total flow rate and at least one of the gradients selected from the utility gradient and the loading gradient at the fast total flow rate.

Embodiments of the present invention further feature a method comprising the steps of determining an elution period in response to the injection of the sample or the anticipated timing of injection of said sample forming at least one concentration gradient in said first volume at a first total flow rate and at a second total flow rate such that the elution period is in the slower of the first total flow rate and the second total flow rate. And, at least one of the utility gradient and the loading gradient is performed during the fast total flow rate. A further embodiment of the present invention is directed to a method of performing chromatographic separations, comprising the step of providing a device having pump means, fluid conveying means, sample injection means, separation means and control means. The control means is in signal communication with the sample injection means and the pump means for controlling the total flow rate and formation of the concentration gradient. The control means monitors the timing or the anticipated timing of the sample injection. The method further comprises the step of determining an elution period in response to the injection of said sample or the anticipated timing of injection of said sample. The method further comprises the step of forming at least one concentration gradient in the first volume at a first total flow rate and at a second total flow rate. And, directing the elution gradient and elution period in the slower of said first total flow rate and said second total flow rate and performing at least one of said utility gradient and said loading gradient in a fast flow period in the fast total flow rate.

Thus, embodiments of the present invention maximize the amount of sample presented to such detectors by reducing the time needed to generate gradient concentrations. Embodiments of the present invention utilize delay volumes inherent in analytical equipment and normally a cause of inefficiency to reduce the time to perform an analysis. These and other advantages and features of the present invention will be apparent upon studying the Drawings and reading the Detailed Description which follow.

DETAILED DESCRIPTION OF EMBODIMENTS OF THE INVENTION

Embodiments of the present invention will be described in detail as methods and apparatus for efficiently performing gradient elution processes with the understanding that features of the present invention have application and utility in industrial processes and diagnostics. With respect to analytical processes, the greater efficiency of chromatographic separation allows detectors to receive more samples and generate more data. Some detectors, such as mass spectrometers, are expensive and it is desirable to operate such instruments to maximise their output of data.

Figure 1:
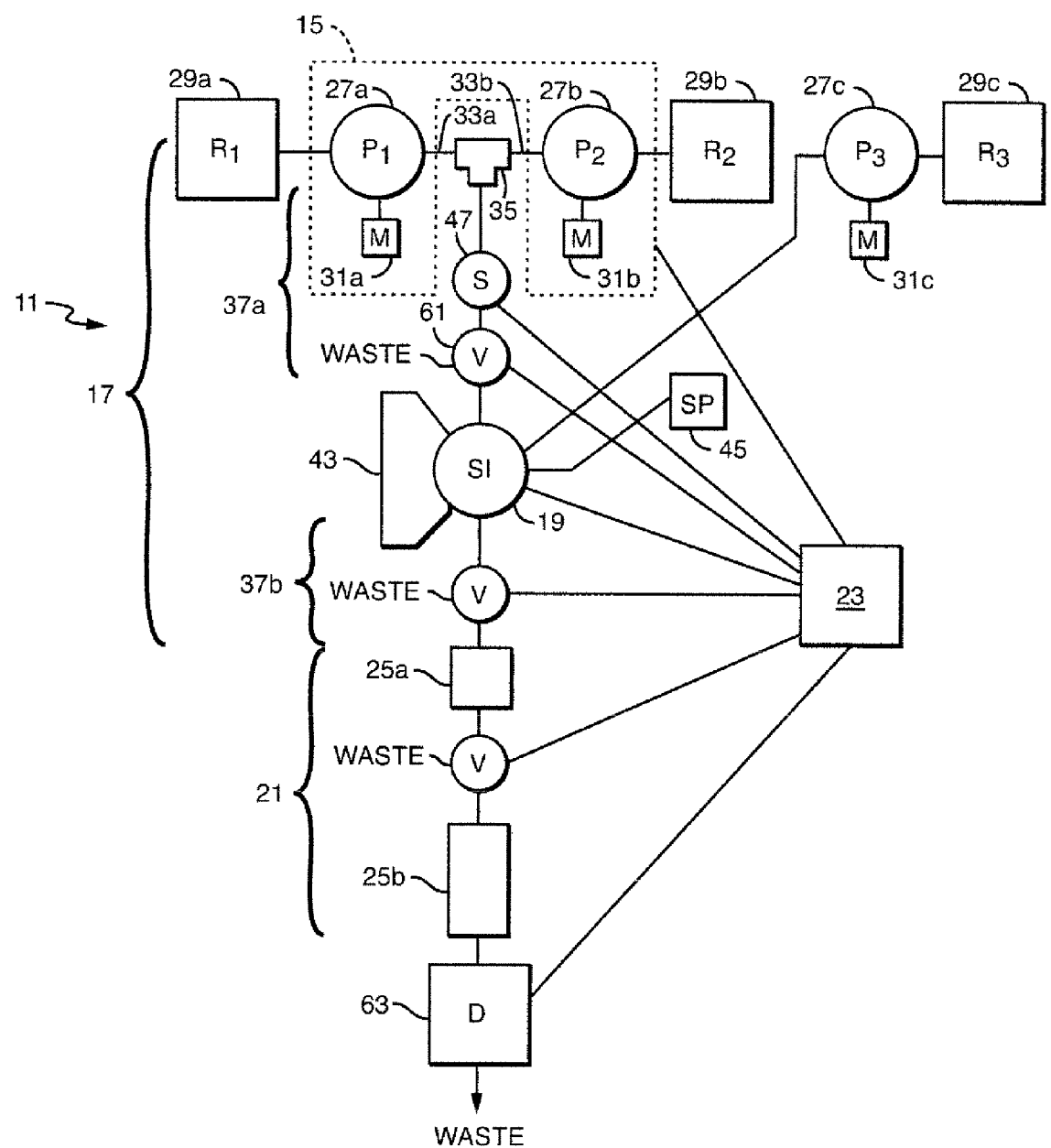
FIG. 1 is a schematic drawing of liquid chromatographic apparatus according to one embodiment of to the invention.

One embodiment of the present invention is directed to a device for performing chromatographic separations. Turning now to FIG. 1, an device for performing chromatographic separations, generally designated by the numeral 11, is depicted. The device 11 has pump means, represented in a dashed box, 15; fluid conveying means, represented by the bracket, 17; sample injection means 19; separation means 21 and control means 23.

The pump means 15 propels a first solvent and a second solvent to form a range of mixtures having a different concentration of the first solvent and the second solvent. The range of mixtures produced by the pump means 15 over time define a concentration gradient. It is common to express the concentration as a volume percentage. This volume percentage may be any group of values that the researcher desires. For example, without limitation, one common group of first solvent and second solvent is water and acetonitrile The first solvent, water, will range in concentration from 3% to 97%, and the second solvent, acetonitrile, will range in concentration from 97% to 3%. Those skilled in the art will recognize that other solvents can be readily substituted for water and acetonitrile. Other solvents by way of example, without limitation, include ethanol, methanol and other alcohols, ketones and ethers.

The range of the concentration gradient will depend on the analysis. The range can have any start or finish. In running a concentration gradient, the user will change the concentration over time. The movement of the first solvent and second solvent define a total flow rate. The pump means 15 is capable of changing the relative concentration of the first and second solvent over time by changing the relative speed at which the first solvent or second solvent is pumped or the proportion of the first and second solvent brought into the pump through a proportioning valve [not shown] known in the art. The combined flow of the first solvent and the second solvent is the total flow rate. The pump means 15 may also change the total flow rate over time.

As depicted, pump means 15 has a first pump 27*a* and a second pump 27*b*. First pump 27*a* and second pump 27*b* are preferably single or dual reciprocating pumps. The first pump 27*a* is in communication with a reservoir 29*a* of a first solvent. And, second pump 27*b* is in communication with a reservoir 29*b* of a second solvent. Preferred dual stage serial pumps are sold under the tradename ALLIANCE® and ACQUITY™ sold by Waters Corporation (Milford, Mass.) and other venders such as Agilent Corporation (Palo Alto, Calif.), Shimadzu Corporation (Japan), Hitachi (Japan) and others. The first pump 27*a* and the second pump 27*b* are powered by a first motor 31*a* and a second motor 31*b* respectively.

The fluid conveying means 17 is in fluid communication with the pump means 15 for receiving the first solvent and the second solvent. The fluid conveying means 17 is comprised of piping, tubing, capillaries, and associated fittings, unions, couplers, "T" unions, valves and the like. Fluid conveying means 17 has a first section 33*a* in fluid communication with first pump 27*a* and a first section 33*b* in fluid communication with second pump 27*b*. The first sections 27*a* and 27*b* join at a "T" union 35. A second section 37, having two parts, a first part 37*a* and a second part 37*b*, extends from the "T" union 35 to the separation means 21. Fluid conveying means 17 has a length and a diameter defining a volume through which the first solvent and the second solvent flow, as a mixture if both first solvent and second solvent are present. This length, as depicted, is the second section 37.

The pump means 15 is capable of forming a concentration gradient along at least a portion of the length of second section 37 in this volume.

The sample injection means 19 is in fluid communication with the fluid conveying means 17. The sample injection means 19 is for placing a sample in at least one of the first solvent and the second solvent flowing through the fluid conveying means 17. As used herein, "sample injection means" refers to a port, sample loop, valve, "T" union, autosampler assembly and the like. As depicted, sample injection means 19 is a multiport valve 41 in fluid communication with sample loop 43 and a sample port 45. Sample port 45, multiport valve 41 and sample loop 43 are preferably part of a autosampler [not shown] known in the art and available from several vendors. One preferred autosampler is sold with pump means 15 under the tradenames ALLIANCE® and ACQUITY™.

Sample is introduced into the sample port 45, multiport valve 41 is rotated to bring the sample port 45 in fluid communication with the sample loop 43. Sample loop 43 receives the sample and multiport valve 41 is reset to bring the sample loop 43 in fluid communication with the second part 37*b* of the second section 37 of fluid conveying means 17.

The separation means 21 is in fluid communication with the fluid conveying means 17 by the second part 37*b* of second section 37. The separation means 21 has at least one separation media [not shown] for receiving the sample and at least one of the first solvent and the second solvent. At least solvent or one range of concentration gradient is a loading gradient in which the sample or compounds of the sample are loaded on the separation media. And, at least one range of concentration gradient is an elution gradient in which one or more compounds are separated over time or in response to changes in the concentration of said first and second solvent. As used herein, the term "elution period" refers to the time in which the elution gradient is performed. And, at least one range of concentration gradient is a utility gradient in which the compounds are conveyed to the separation means, or the separation means are conditioned for sample.

Separation means 21 refers to columns, extraction cartridges, and other in-line closed devices known in the art. Separation media refers to particles, porous monolith materials, and other packings known in the art. Columns and extraction cartridges are sold by several vendors. Preferred separations means 21 are columns sold under the trademarks EXTERRA™, OASIS®, ATLANTIS™ and SYMMETRY®. As depicted, separation means comprises a trapping column 25*a* and a analytical column 25*b*. Trapping column 25*a* is a shorter column designed to initially capture the compounds of interest. Analytical column 25*b* is intended to perform a separation of the compounds of interest.

Control means 23 is in signal communication with the sample injection means 19 and the pump means 15 for controlling the total flow rate and formation of the concentration gradient. The control means 23, in response to the injection of the sample or the anticipated timing of the injection of the sample, determines and forms at least one concentration gradient in the volume of the fluid conveying means 17 at a fast total flow rate and at a slow total flow rate. Control means 23 determines the start of the slow flow rate such that the elution gradient passes through the separation media during an elution period in the slow total flow rate, and at least one of the utility gradient and the loading gradient occurs during a fast period in the fast total flow rate.

Control means 23 refers to one or more computer processing units (CPUs), personal or main frame computers equipped with suitable software or firmware. Software packages are available from several vendors that provide tools to allow the user to program control means 23 in the manner described. A preferred software package is sold under the trademark EMPOWER™ (Waters Corporation, Milford, Mass.). Computer processing units, in the form of personal computers and servers are available from several vendors. A preferred control means 23 is sold as part of pump means 15 and sample injection means 19 under the trademarks ALLIANCE® and ACQUITY™.

Embodiments of the present invention use volumes normally associated with delay, that is, such volumes in the fluid conveying means 17, to build and store concentration gradients. At slow flow rates, such delays, often referred to as gradient delays, can be substantial.

Preferably, control means 23 automatically determines a fast period and a slow period. The user is expected to know from experience or due to the nature of the compounds that the compounds of interest will elute in the slow period. That is, the elution period is anticipated or known to fall in the slow period. Although it is desirable to have the slow period limited to the elution period, it is expected that a period extending before and after the elution period will be in the slow period.

Figure 2A:
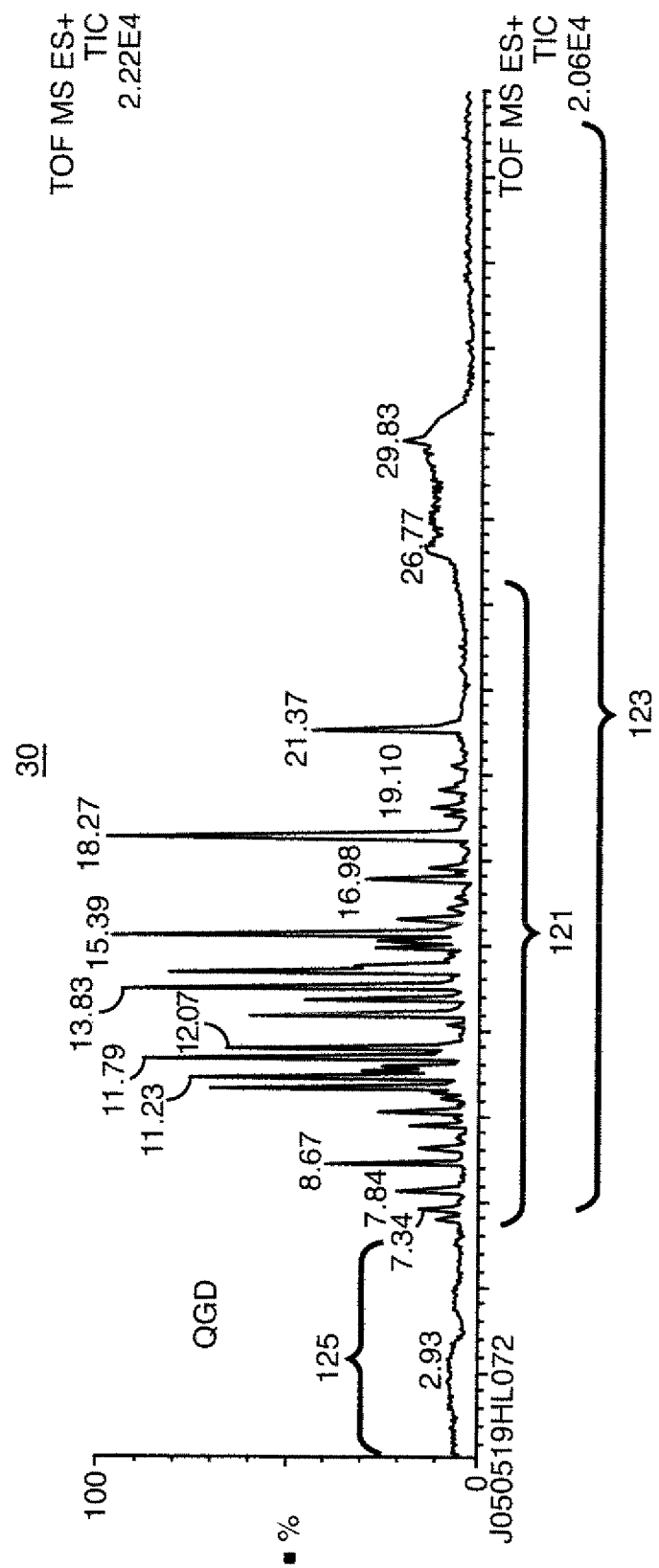
FIG. 2A is a liquid chromatogram (identified as "QGD") obtained from a sample comprising 100 fmol of enolase digest using a nanoflow chromatographic column and using a method of the invention and the apparatus shown schematically in FIG. 1.
Figure 2B:
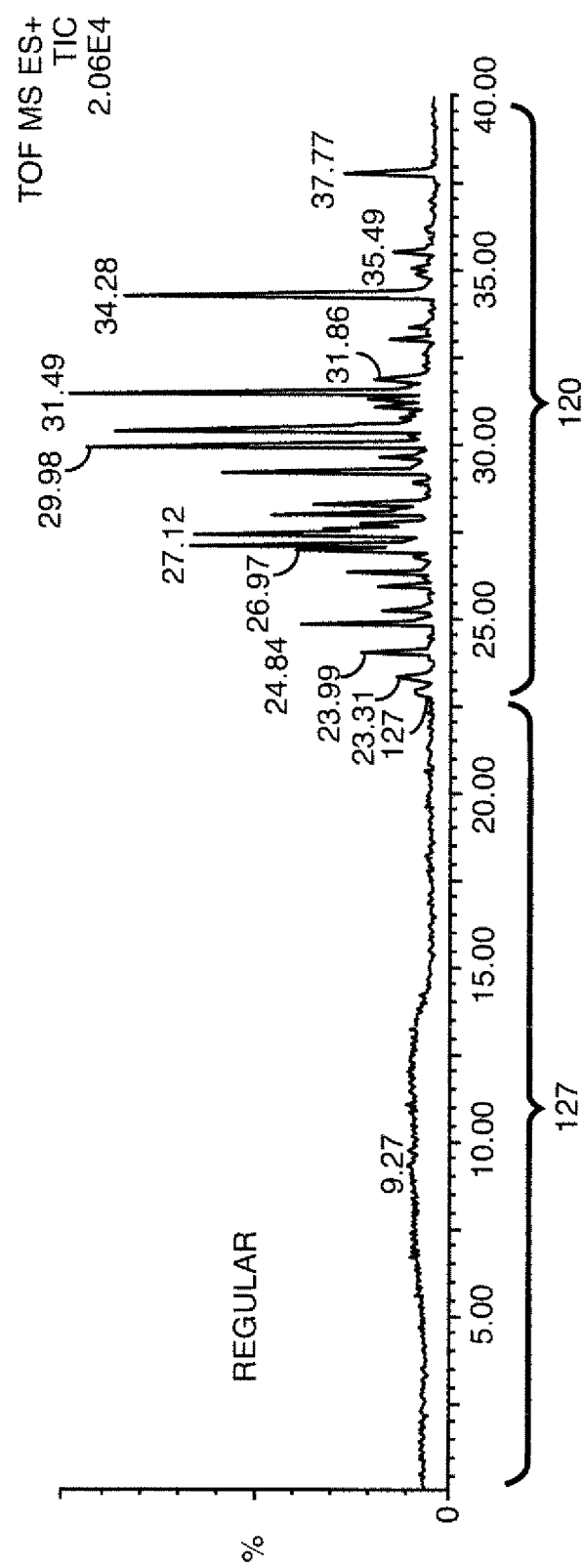
FIG. 2B is a liquid chromatogram (identified as "Regular") obtained from a sample similar to that used to obtain the chromatogram of FIG. 2A, without the benefit of any method or apparatus according to the invention.

Turning briefly to FIG. 2B, a chromatogram performed with a concentration gradient at a single analytical flow rate is depicted. The concentration of peaks in area of the bracket 120 represents the compounds of interest eluting. That is, the bracket area 120 is the elution period. The user will understand from this data that there is a concentration range at which these compounds elute. The chromatogram shown in FIG. 2A is performed with a concentration gradient in which part of the gradient is at first a fast flow rate and part of the gradient is at a slow flow rate. The elution period is represented by the area defined by bracket 121 within a slow period defined by bracket area 123. The fast period is the area defined by bracket 125. The FIG. 2A chromatogram is essentially completed after the elution period 121 and can repeat the process. The time at which the elution period is completed is significantly earlier than for the process operated at a single analytical flow rate. The elution period for the single flow rate process depicted in the FIG. 2B chromatogram is just beginning, following a long period represented by the bracket area 127 of approximately 25 minutes. At this time, the elution period 121 represented in the FIG. 2A chromatogram is finished. These results are surprising and striking with little or no loss in separation quality.

Embodiments of the present device are well suited for handling a plurality of samples in an automated manner. For example, the control means 23 is programmed to repeat the concentration gradient for a plurality of samples in which each concentration gradient is a gradient cycle substantially next to at least one preceding or subsequent concentration gradient in the fluid conveying means. The time saving represented by the present invention greatly increases the efficiency of the analytical process.

The slow period, in which the elution period will occur, and the fast period, for a linear gradient performed between Bx to By, are determined in accordance with the following relationships:

$$T_{qgd} = V_d / F_{qgd} \quad \text{(Formula I)}.$$

As used above, $T_g$ is the time at the slow total flow rate of $F_g$ to complete the linear gradient between Bx and By. The designation, Bx, is used to denote the lowest, and, By, the highest concentration in percentage, of a selected solvent selected from the group of the first solvent and second solvent. The letter designation, $T_{qgd}$, is the time needed to perform said fast period. The letter designation, $V_d$, is the volume of the fluid conveying means and $F_{qgd}$ is the flow rate of the fast period. And, the control means determines $B_{qgd}$, the highest concentration of the selected solvent to be delivered during the fast period, in accordance with Formula II, set forth below:

$$B_{qgd} = [V_d(B_y - B_x) / F_g T_g] + B_x \quad \text{(Formula II)}.$$

And, the slow period, $T_2$, is determined by Formula III below:

$$T_2 = T_g - (V_d / F_g) \quad \text{(Formula III)}.$$

The elution period occurs in the slow period. And, the time to complete the fast period, $T_{combined}$, is determined with the following Formula IV:

$$T_{combined} = T_2 + T_{qgd} \quad \text{(Formula IV)}.$$

Preferably, control means 23 uses a value of $V_d$ selected from the group of values consisting of an assigned value and a calculated value. For example, a preferred control means 23 has memory [not shown] commonly associated with computers and CPUs, such as hard-drives, memory chips and other memory devices. An assigned value or a calculated value is stored in such memory. The assigned value can be approximated based on internal measurements of the fluid conveying means 17 and stored in the memory during a manufacturing process or other convenient times.

One embodiment of the present invention features a calculated value determined by the relationship, as set forth below:

$$V_d = F_c (T_{c1} - T_{c2}) \quad \text{(Formula V)}.$$

As used above, $F_c$ is the flow rate at a stable back pressure of a high percentage concentration of the second solvent represented by $B_{high}$; and $T_{c1}$ is the time at which such second solvent is changed to a low percentage concentration $B_{low}$ and $T_{c2}$ is the time that the back pressure at such low percentage concentration becomes stable.

A preferred control means 23 calculates a value of $V_d$ upon receiving instructions to do so from an operator, or automatically, when the operator designates a fast gradient operation, or if there is no preset value which the control means can use.

To facilitate the calculation of the value of $V_d$, one embodiment features at least one of the pump means 15 and fluid conveying means 17 having a pressure sensor. Pressure sensors are often integrated into the pump mechanics and can be used for this purpose. A pressure sensor 47 is depicted in the first part 37a of second section 37 of fluid conveying means 17. The pressure sensor 47 is in signal communication with the control means 23 to measure pressure in the fluid components.

Preferably, the fast total flow rates are four to one hundred times the flow rates of slow total flow rates. At such fast flow rates, the pump means 15 and the fluid conveying means 17 may develop high pressures. Pump means 15 and fluid conveying means 17 typically have a maximum safe operating pressure at operation will not cause mechanical breakdown. Preferably, the pressure sensor 47 produces a signal in respond to pressures greater than such safe operating pressure.

In the alternative or in addition to such pressure sensor warning, one embodiment of the present invention features control means 23 that calculates an anticipated pressure for the fast total flow rate and compares the anticipated pressure to a safe operating pressure value. The control means 23 produces a stop or warning signal in response to the anticipated pressure exceeding said safe operating pressure value.

Device 11 has an exit port 51. The exit port 51 is fluid communication with the second part 37b of the second section 37 of the fluid conveying means 17 upstream of the separation means 21. The exit port 51 is in signal communication with the control means 23 to receive commands to assume at least one of two positions. The exit port 51 has an open position and a closed position. In the closed position, the exit port 51 directs the first solvent, second solvent and, if present, sample, to the separation means 21. And, in the open position, the exit port 51 directs the first solvent, second solvent and, if present, sample, to waste.

The exit port 51 allows the pump means 15 to increase the flow rate without the resistance of the separation means 21 and resultant increase in pressure. Exit port 51 reduces wear on pump means 15, sample injection means 19 and the separation means 21.

As depicted in FIG. 1, separation means 21 comprising a trapping column 25a and analytical column 25b. One embodiment of the present invention features a solvent port 55 that cooperates with a separation means 21 comprising a trapping column 25a and an analytical column 25b. The solvent port 55 is in fluid communication with the fluid conveying means 17. The solvent port 55 is upstream from the trapping column 25a and is in fluid communication with a third solvent represented by third solvent reservoir 29c. The third solvent represented by third solvent reservoir 29c is capable of releasing the compound or compounds of interest from the trapping column 25a. The released compound or compounds are carried to the analytical column 25b which analytical column 25b effects separation. Fluid is compelled through solvent port 55 by a third pump 27c.

The solvent port 55 is in the nature of a valve having an open position in which the port communicates with the conveying means 17 and a closed position in which it does not. The solvent port 55 and third pump 27c are in signal communication with control means 23 to coordinate the activation of third pump 27c with the position of the solvent port 55.

As depicted, the separation means comprises a shunt valve 57. Shunt valve 57 is interposed, in fluid communication, between the trapping column 25a and the analytical column 25b. Shunt valve 57 is in signal communication with control means 23 and has an open position and a closed position. Control means 23 commands the shunt valve 57 to assume the open position in which fluid is directed to waste during the period in which the sample is loaded on the trapping column 25a. Control means 23 commands the shunt valve 57 to close during the release of the compounds of interest from the trapping column 25a. The operation of the shunt valve 57 is coordinated with the solvent port 55 and third pump 27c by control means 23.

The control means 23 sends a signal to the solvent port 55 to assume an open position and release the third solvent. At the same time, the control means sends a signal to the shunt valve 57 to close. During the time the sample is loaded on the analytical column, control means 23 begins forming a concentration gradient in the fluid conveying means 17.

The fluid conveying means 17 has a gradient port 61. Gradient port 61 has an open position in which fluid is directed to waste and a closed position in which fluid is carried forth in the fluid conveying means 17. Gradient port 61 is in signal communication with control means 23. Control means 23 sends a command signal to direct gradient port 61 to assume one of the two positions. In the open position, a concentration gradient is formed in the upstream portion of fluid conveying means 17.

It will be recognised by those skilled in the art that the ports and valves of the present device can be consolidated into one or more multiport valves. The depictions of the fluidic paths in FIG. 1 have been simplified for illustrative purposes.

As illustrated, the device 11 comprises detection means 63 in fluid communication with the separation means 21. The detection means 63 receives the sample or compounds of the sample and produces an analytical signal during the analytical period. This analytical signal is received by control means 23 or other memory devices known in the art [not shown] and or computing systems. The detection means 63 may assume any number of detectors known in the art. By way of example, without limitation, detection means may comprise photodetectors, such as photodiode array detectors, Ramon light detectors, light scattering detectors, light absorbance detectors, fluorescence detectors, chemiluminescent detectors, or electrochemical detectors, mass detectors, nuclear magnetic resonance detectors and others.

A further embodiment of the present invention, directed to a method of performing chromatographic separations, will be described with respect to the operation of the device 11. The method comprising the steps of providing a device 11 as described in any of the embodiments above and operating the device to produce a concentration gradient at a fast total flow rate and a slow total flow rate in response to the injection of a sample or the anticipated injection of said sample. The present method performs the step of elution during a calculated elution period at the fast total flow rate and at least one of the gradients selected from the utility gradient and the loading gradient at the slow total flow rate.

Embodiments of the present invention further feature a method wherein the user performs the calculation of an elution period in response to the injection of said sample or the anticipated timing of injection of said sample. And, the user forms at least one concentration gradient in the first volume at a first total flow rate and at a second total flow rate such that the elution period occurs during the slower of said first total flow rate and the second total flow rate, and at least one of the utility gradient and the loading gradient is performed in a fast flow period in the fast total flow rate.

The method of performing chromatographic separations, comprising the step of providing a device having pump means, fluid conveying means, sample injection means, separation means and control means. The control means 23 is in signal communication with the sample injection means 19 and the pump means 15 for controlling the total flow rate and formation of the concentration gradient. The control means 23 has a timing element for monitoring the timing of the sample injection. The method further comprises the step of determining an elution period in response to the injection of the sample or the anticipated timing of injection of the sample. The method further comprises the step of forming at least one concentration gradient in the first volume at a first total flow rate and at a second total flow rate. And, the method includes the step of directing the elution period in the slower of said first total flow rate and said second total flow rate, and performing at least one of the utility gradient and the loading gradient in a fast flow period in the fast total flow rate.

Typically the sample loop 43 may have a volume of 2 µl and chromatographic column 25b is a "nanoflow" column. A suitable column may be a "ACQUITY" column, 75 µm diameter and 10 cm long, packed with 3 µm particles of Atlantis $C_{18}$, available from Waters Corporation, Milford, Mass., USA, but other types of columns may be used as required for different chromatographic separations. For "nanoflow" chromatography, the pump means 15 should be capable of delivering a stable flow of less than 1 µl/minute at pressures and more preferably 500 nl/minute as high as 5,000-15,000 psi, and the volume of the liquid conveying means 17 should be as low as possible (typically less than 5 µl, including the sample valve 19 and loop 43). A suitable pumping system is the nano ACQUITY UPLC system, available from Waters Corporation, Milford, Mass.

In the example apparatus illustrated in FIG. 1, this internal volume may be of the order of 5 µl when a typical sample loop 43 of volume 2 µl is employed. In pumping systems 15 designed for very low flow rates, this internal volume will be as small as possible. As explained, an internal volume of 5 µl can result in a gradient delay of 20 minutes, with a flow rate of 250 nl/minute, while the internal volume is filled.

Referring now to FIGS. 2A and 2B, the FIG. 2B chromatogram (identified as "Regular") is a chromatogram obtained under such conditions using an electrospray ionization mass spectrometer as a detector 63. The sample analyzed comprised 100 fmol. of an enolase digest and the chromatographic column was a Waters "ACQUITY" column, 75 µm diameter 10 cm long packed with 3 µm Atlantis $C_{18}$ particles. Solvent A comprised 0.1% formic acid in water and solvent B comprised 0.1% formic acid in acetonitrile. The gradient parameters shown in Table 1 were used.

TABLE 1

| Time (minutes) | Flow rate (nl/minute) | % A | % B |
|---|---|---|---|
| 0 | 250 ($F_g$) | 97 | 3 ($B_x$) |
| 30 ($T_g$) | 250 | 40 | 60 ($B_y$) |
| 50 | 250 | 97 | 3 |

The retention time of the first peak 129 appearing in the chromatogram of FIG. 2B is approximately 23 minutes, of which approximately 20 minutes in a gradient delay due to the internal volume of the liquid conveying means 17. In order to reduce this gradient delay, the gradient parameters shown in Table 2 were employed to generate the chromatogram shown in FIG. 2A (identified as "QGD").

TABLE 2

| Time (minutes) | Flow Rate (nl/minute) | % A | % B |
|---|---|---|---|
| 0 | 1000 | 97 | 3 ($B_x$) |
| 5 | 1000 ($F_{qgd}$) | 59 | 41 ($B_{qgd}$) |
| 5.01 | 250 ($F_g$) | 59 | 41 |
| 15 ($T_2 + T_{qgd}$) | 250 | 40 | 60 ($B_y$) |
| 35 | 250 | 97 | 3 |

Comparing the chromatograms shown in FIGS. 2A and 2B, it is seen that the gradient delay 125 in the "QGD" chromatogram (FIG. 2A) is much shorter than the corresponding delay 127 in the "Regular" chromatogram (FIG. 2B), while the portions of the two chromatograms where the major sample constituents elute, (respectively indicated at 120 and 121) is largely unaffected. In this way the total analysis time is reduced from 50 minutes using the Table 1 parameters to 35 minutes using the Table 2 parameters, without significantly affecting the resolution or sensitivity of the relevant part of the chromatogram.

Figure 3A:
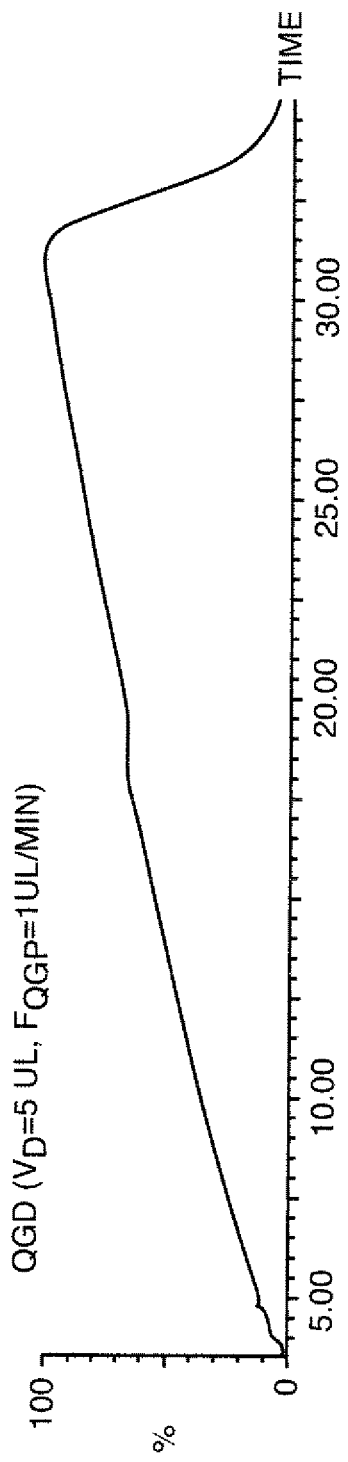
FIG. 3A is the gradient profile observed for the chromatogram shown in FIG. 2A.
Figure 3B:
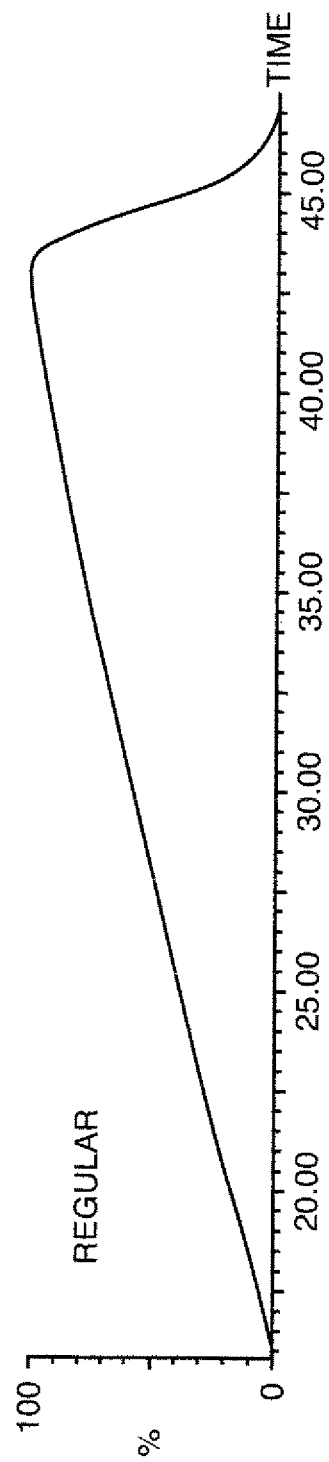
FIG. 3B is the gradient profile observed for the chromatogram shown in FIG. 2B.

FIGS. 3A and 3B respectively show the observed gradient profiles for the chromatograms of FIGS. 2A and 2B. The FIG. 3A profile (identified as "QGD") is that obtained using the parameters listed in Table 2, and the FIG. 3B profile (identified as "Regular") is that obtained using the parameters listed in Table 1. It can be seen that the two profiles are very similar, showing that using the method of the invention does not appreciably change the profile used for the separation. However, the "QGD" profile is obtained much sooner than the "Regular" profile.

The parameters listed in the Table 2 may be arrived at through the Formulas I-IV, as set forth previously.

The values for $F_g$, $T_g$, $B_0$ and $B_g$ are set forth in Table 1, and FIG. 2. The internal volume $V_d$ of the liquid conveying means 17 is determined by any suitable method including measuring and calculating the interior area of liquid conveying means 17 or through Formula V. A value of 5 microliters was determined in this example. A value of the second flow rate $F_{qgd}$ is selected, typically in the range 4-10 times the flow rate $F_g$ the elution period is desired. The Table 2, $F_g$ is 250 µl/minute, $F_{qgd}$ is 1000 n/minute. The selected value of $F_{qgd}$ must be such that the maximum pressure built up in the liquid-conveying means 17 does not exceed the maximum pressure which pumps means 15 is capable of delivering. This maximum value for $F_{qgd}$ is determined by experiment for any particular combination of pumps means 14, solvents and separation means 21. The higher the selected value of $F_{qgd}$, the more the gradient delay can be reduced and the faster the total separation may take place.

Next, the time needed to perform the fast period, $T_{qgd}$, that pump means 15 should deliver the second flow rate $F_{qgd}$ is found from the equation:—

$$T_{qgd} = V_d / F_{qgd}$$

In the example of Table 2, $V_d$ is 5 µl and $F_{qgd}$ is 1000 nl/minute, so that $T_{qgd}$=5 minutes. $T_{qgd}$ is in effect the time taken to fill the volume $V_d$ at the flow rate $F_{qgd}$.

This example describes the chromatographic separation using the same gradient profile and flow rate (listed in Table 1) used to obtain the conventional chromatogram of FIG. 2, it is not necessary to calculate the actual profiles to be generated both during $T_{qgd}$ and subsequently. The complete gradient used in Table 1, ($B_x$–$B_y$) is delivered in time $T_g$ and occupies a volume of 7.5 µl ($F_g \times T_g$). Accordingly, 5 µl of this gradient is actually stored in the internal volume $V_d$ at a flow rate of 1000 nl/minute, ($F_{qgd}$) during the time of 5 minutes ($T_{qgd}$). The actual percentage of solvent B to be reached at the end of this period ($B_{qgd}$) is given by $$B_{qgd} = [V_d(B_y - B_x)/F_g T_g] + B_x \qquad \text{Formula II}$$

In this example, $$B_{qgd} = [5000(60 - 3)/(250 \times 30)] + 3$$
$$= 41\%$$

Control means 23 is therefore programmed to deliver 41% of solvent B after 5 minutes.

The remaining part of the gradient still to be generated should now be selected so that after $T_{qgd}$ has elapsed, the percentage of solvent B should increase to $B_g$ during a second time interval $T_2$ at the flow rate of $F_g$. $T_2$ is given by the equation:

$$T_2 = T_g - (V_d / F_g) \qquad \text{Formula III}$$

Which in this example reduces to $$T_2 = 30 - 5000/1000 = 10 \text{ minutes.}$$

These parameters are also programmed into the control means 23, as shown in Table 2.

The example method described above is appropriate when it is desired to convert an existing conventional gradient profile which results in a long gradient delay to a new profile according to the invention without significantly affecting the quality of the chromatogram. However, other embodiment is of the invention do not require the flow rate used in the second portion of the analysis to be the same as that used to obtain the conventional chromatogram ($F_g$). Methods may of course be developed according to the invention which do not reference a prior conventional chromatographic separation. Embodiments of the invention may comprise the generation of an initial gradient profile at an initial flow rate in order to at least partially fill the volume $V_d$, and the subsequent production of a second gradient at a lower flow rate in order to carry out the chromatographic separation. The extent of the reduction in gradient delay time that can be achieved will of course be limited by the maximum pressures that can be generated by pump means 15 and fluid conveying means 17, which may limit the proportion of the gradient that can be stored in the internal volume $V_d$.

In other embodiments of the invention the gradients employed may comprise three or more portions in which at least one of the initial portions is generated at a higher flow rate than that used to generate at least one of the later portions. Such initial portions would generally be such that the total volume of the gradient generated would be smaller than the internal volume $V_d$. The parameters for such a separation could be calculated in a similar way to that outlined for the two-portion system outlined above.

The internal volume $V_d$ of the liquid-conveying means 17 may be an approximate value. For example, it will usually suffice to calculate $V_d$ by adding the volumes such as the pipes fitting and the like that comprise liquid conveying means 17. A typical device 11 has a total of 4160 microliters. However, a value of 5 μl was used to calculate the parameters of Table 2. The approximation is acceptable because the sample cannot be lost even if the volume $V_d$ is overfilled during the initial phase, assuming that the maximum pressure that the pump can deliver is not exceeded. Rather, it would simply be swept onto the separation means 21 at the higher initial flow rate. Similarly, if the volume $V_d$ is only partially filled during the initial phase, the only effect will be that the reduction in gradient delay may be less than might otherwise be achieved.

An experimental method by which $V_d$ may be determined is as follows. First, a mobile phase having a high proportion of solvent B (e.g. 85%) is pumped through the chromatographic column until the backpressure at the pump has become stable. The composition of the mobile phase is then changed to a low percentage of solvent B (eg, 3%), and the time $T_1$ of this change recorded. The backpressure is then observed, and the time $T_2$ at which it begins to change (as a result of the changed composition of the mobile phase reaching the column) is recorded. The volumes $V_d$ may then be found from the equation:

$$V_d = F(T_2 - T_1)$$

Where F is the flow rate.

The value of $V_d$, determined by the manufacturer, may also be stored in memory associated with the apparatus, so that a user is not required to estimate its value.

One embodiment of the present invention is directed to software and/or hardware that may automatically calculate the parameters needed to convert a conventional gradient-elution chromatographic separation to one with reduced gradient delay, conveniently by means of the equations described above. The software may be programmed on the separation instrument to make a device 11.

Thus, the present invention have been described with respect to what is considered to be the preferred embodiments, with the understanding that the invention is subject to modification and alteration without departing from the teaching and disclosure herein. Therefore, the present invention should not be limited to the precise details set forth in the description but should include the subject matter of the claims that follow and their equivalents.

What is claimed is:

1. A device for performing chromatographic separations, comprising;
   a. pump means, said pump means for propelling a first solvent and a second solvent to form a range of mixtures having a different concentration of said first solvent and said second solvent, said range of mixtures over time defining a concentration gradient, said first solvent and second solvent defining a total flow rate capable of being changed over time;
   b. a fluid conveying means in fluid communication with said pump means for receiving said first solvent and said second solvent, said fluid conveying means having a length and a diameter defining a volume through which said first solvent and said second solvent flow, as a mixture if both first solvent and second solvent are present, said pump means capable of forming a concentration gradient along at least a portion of the length in said volume;
   c. sample injection means in fluid communication with said fluid conveying means for placing a sample in at least one of said first solvent and said second solvent flowing through said fluid conveying means;
   d. separation means in fluid communication with said fluid conveying means comprising at least one separation media for receiving said sample and at least one of said first solvent and said second solvent in which at least one solvent or one range of concentration gradient is a loading gradient in which said sample or compounds of said sample are loaded on said separation media, and at least one range of concentration gradient is a elution gradient in which one or more compounds are separated over time or in response to changes in the concentration of said first and second solvent said elution gradient being performed during an elution period, and at least one range of concentration gradient is a utility gradient in which the compounds are conveyed to the separation means, or the separation means are conditioned for sample; and,
   e. control means in signal communication with said sample injection means and said pump means for controlling the total flow rate and formation of said concentration gradient, said control means monitoring the timing of said sample injection and in response to the injection of said sample or the anticipated timing of said injection of said sample, determining and forming at least one concentration gradient in said volume at a fast total flow rate and at a slow total flow rate such that said elution gradient passing through said separation media during an elution period is at the slow total flow rate, and at least one of said utility gradient and said loading gradient occurring during a fast period in the fast total flow rate.

2. The device of claim 1 wherein said control means determines a fast period and the elution period for a linear gradient performed between Bx to By in accordance with the following relationships:

$$T_{qgd} = V_d / F_{qgd}$$

where $T_g$ is the time at said slow total flow rate of $F_g$ to complete the linear gradient between Bx and By, Bx is the lowest and By is the highest concentration in percentage of a selected solvent selected from the group of the first solvent and second solvent, $T_{qgd}$ is the time needed to perform said fast period, $V_d$ is the volume of the first conveying means, $F_{qgd}$ is the flow rate of the fast period, and $$B_{qgd} = [V_d(B_y - B_x)/F_g T_g] + B_x,$$

where $B_{qgd}$ is the highest concentration of the selected solvent to be delivered during the fast period, and, $$T_2 = T_g - (V_d / F_g),$$

where $T_2$ is the slow period and $T_{combined}$ is the time to complete the fast period and the elution period wherein $$T_{combined} = T_2 + T_{qgd}.$$

3. The device of claim 2 wherein $V_d$ is selected from the group of values consisting of an assigned value and a calculated value.

4. The device of claim 3 wherein said control means has memory and said assigned value is store therein.

5. The device of claim 3 wherein said calculated value is determined by the relationship:

$$V_d = F_c(T_{c1} - T_{c2})$$

Wherein $F_c$ is the flow rate at a stable back pressure of a high percentage concentration of said second solvent represented by $B_{high}$ and $T_{c1}$ is the time at which such second solvent is changed to a low percentage concentration $B_{low}$ and $T_{c2}$ is the time that the back pressure at such low percentage concentration becomes stable.

6. The device of claim 1 wherein at least one of said pump and fluid conveying means has pressure sensors which pressure sensors are in signal communication with said control means to measure pressure in said device.

7. The device of claim 6 wherein said control means calculates $V_d$ in response to a direction from the operator or automatically with the operator instructions to perform a fast gradient.

8. The device of claim 6 wherein said device has a maximum safe operating pressure and said pressure sensor produces a signal in respond to pressures greater than said safe operating pressure.

9. The device of claim 1 wherein said control means repeats said concentration gradient for a plurality of samples in which each concentration gradient is a gradient cycle substantially next to at least one preceding or subsequent concentration gradient in said first conveying means.

10. The device of claim 1 wherein said fluid conveying means comprises a port, said port in signal communication with said control means and having an open position and a closed position, in said closed position said port directs said first solvent, second solvent and, if present, sample, to said separation means and in said open position, said port directs said first solvent, second solvent and, if present, sample, to waste.

11. The device of claim 1 wherein said control means calculates an anticipated pressure for the fast total flow rate and compares said anticipated pressure to a safe operating pressure value.

12. The device of claim 11 wherein said control means produces a stop signal in response to said anticipated pressure exceeding said safe operating pressure value.

13. The device of claim 1 wherein said fast total flow rate is at least about four times faster than the slower total flow rate.

14. The device of claim 1 wherein said separation means comprises a trapping column and an analytical column.

15. The device of claim 14 wherein said fluid conveying means has a solvent port, said solvent port in fluid communication with a third solvent, said third solvent for releasing one or more compounds from said trapping column.

16. The device of claim 15 wherein said solvent port is in signal communication with said control means, said control means sending a release signal to said solvent port to release said third solvent to release said one or more compounds to said analytical column.

17. The device of claim 16 wherein said control means begins said elution period after said release signal.

18. The device of claim 1 further comprising detection means in fluid communication with said separation means for receiving said sample or compounds of said sample and producing a analytical signal, said time in which said detection means receiving sample or compounds of said sample forming an analytical period.

* * * * *